(12) United States Patent
Whitman

(10) Patent No.: US 6,533,157 B1
(45) Date of Patent: Mar. 18, 2003

(54) TISSUE STAPLING ATTACHMENT FOR USE WITH AN ELECTROMECHANICAL DRIVER DEVICE

(75) Inventor: Michael P. Whitman, New Hope, PA (US)

(73) Assignee: Power Medical Interventions, Inc., New Hope, PA (US)

( * ) Notice: Subject to any disclaimer, the term of this patent is extended or adjusted under 35 U.S.C. 154(b) by 0 days.

(21) Appl. No.: 09/510,931

(22) Filed: Feb. 22, 2000

(51) Int. Cl.$^7$ .............................................. A61B 17/04
(52) U.S. Cl. ...................... 227/175.1; 227/19; 227/83; 227/88; 227/89; 227/176.1; 227/177.1
(58) Field of Search .............................. 227/19, 83, 88, 227/89, 176.1, 175.1, 177.1

(56) References Cited

U.S. PATENT DOCUMENTS

| 3,079,606 A | 3/1963 | Bobrov et al. |
| 3,193,165 A | 7/1965 | Akhalaya et al. |
| 3,256,875 A | 6/1966 | Tsepelev et al. |

(List continued on next page.)

FOREIGN PATENT DOCUMENTS

| DE | 29 03 159 | 7/1980 |
| DE | 3300768 | 1/1983 |
| DE | 33 00 768 | 7/1984 |
| EP | 0 593 920 | 4/1974 |
| EP | 0 116 220 | 8/1984 |
| EP | 0 121 474 | 10/1984 |
| EP | 0 142 225 | 5/1985 |
| EP | 0 156 774 | 10/1985 |
| EP | 0 203 375 | 12/1986 |
| EP | 0 216 532 | 4/1987 |
| EP | 0 399 701 | 11/1990 |
| EP | 0 514 139 | 11/1992 |
| EP | 0 536 903 | 4/1993 |
| EP | 0 539 762 | 5/1993 |
| EP | 0 552 050 | 7/1993 |
| EP | 0 621 006 | 10/1994 |
| EP | 0 634 144 | 1/1995 |
| GB | 2 044 108 | 10/1980 |
| GB | 2180455 | 4/1987 |
| NL | 77 11 347 | 4/1979 |
| WO | WO 90/05491 | 5/1990 |
| WO | WO 92/16141 | 10/1992 |
| WO | WO 93/08754 | 5/1993 |
| WO | WO 93/14706 | 8/1993 |
| WO | WO95/18572 | 7/1995 |
| WO | WO95/35065 | 12/1995 |

*Primary Examiner*—Rinaldi I. Rada
*Assistant Examiner*—Louis Tran
(74) *Attorney, Agent, or Firm*—Kenyon & Kenyon

(57) ABSTRACT

A stapler attachment for use with an electromechanical device driver comprises a staple holding member which is spring mounted to a staple closing member, which is, in turn, mounted to a threaded driver element concentrically mounted about a threaded shaft such that staple closing member and the staple holding member can be advanced and retracted along a track within a housing. A staple is advanced by the rotation of the threaded shaft until the staple holding member is stopped against an opening lip formed in an opening at the distal staple discharging end of the housing. At this position, the prongs of the staple have been advanced out of the distal staple discharging end and into the tissue to be joined. The staple closing member continues to advance as the spring between the staple holding member and the staple closing member compresses. This advancement permits the staple closing member to deform the staple into a closed D-shape conformation. The staple is released from the attachment through the distal staple discharging end of the housing upon further advancement of the staple closing member. Reverse rotation of the threaded shaft retracts the staple closing member and staple holding member into a staple receiving position where a spring-loaded staple dispenser pushes one of a plurality of staples in a staple cartridge into a staple carrying groove of a staple carrying element of the staple holding member, in preparation for a subsequent stapling procedure.

11 Claims, 4 Drawing Sheets

U.S. PATENT DOCUMENTS

| | | |
|---|---|---|
| 3,388,847 A | 6/1968 | Kasulin et al. |
| 3,490,675 A | 1/1970 | Green et al. |
| 3,494,533 A | 2/1970 | Green et al. |
| 3,552,626 A | 1/1971 | Astafiev et al. |
| 3,618,842 A | 11/1971 | Bryan |
| 3,662,939 A | 5/1972 | Bryan |
| 3,815,476 A | 6/1974 | Green et al. |
| 3,858,577 A | 1/1975 | Bass et al. |
| 3,859,986 A | 1/1975 | Okada et al. |
| 4,071,029 A | 1/1978 | Richmond et al. |
| 4,085,756 A | 4/1978 | Weaver |
| 4,198,960 A | 4/1980 | Utsugi |
| 4,198,982 A | 4/1980 | Fortner et al. |
| 4,202,479 A | 5/1980 | Razgulov et al. |
| 4,207,898 A | 6/1980 | Becht |
| 4,250,873 A | 2/1981 | Bonnet |
| 4,273,109 A | 6/1981 | Enderby |
| 4,273,111 A | 6/1981 | Tsukaya |
| 4,289,131 A | 9/1981 | Mueller |
| 4,289,133 A | 9/1981 | Rothfuss |
| 4,304,236 A | 12/1981 | Conta et al. |
| 4,310,115 A | 1/1982 | Inoue |
| 4,319,576 A | 3/1982 | Rothfuss |
| 4,331,277 A * | 5/1982 | Green ..................... 227/130 |
| 4,334,539 A | 6/1982 | Childs et al. |
| 4,351,466 A | 9/1982 | Noiles |
| 4,367,729 A | 1/1983 | Ogiu |
| 4,379,457 A | 4/1983 | Gravener et al. |
| 4,402,311 A | 9/1983 | Hattori |
| 4,410,125 A * | 10/1983 | Noiles et al. ............. 227/145 |
| 4,429,695 A | 2/1984 | Green |
| 4,442,964 A | 4/1984 | Becht |
| 4,445,509 A | 5/1984 | Auth |
| 4,445,892 A | 5/1984 | Hussein et al. |
| 4,448,188 A | 5/1984 | Loeb |
| 4,473,077 A | 9/1984 | Noiles et al. |
| 4,476,863 A | 10/1984 | Kanshin et al. |
| 4,485,817 A | 12/1984 | Swiggett |
| 4,487,270 A | 12/1984 | Huber |
| 4,488,523 A | 12/1984 | Shichman |
| 4,489,724 A | 12/1984 | Arnegger |
| 4,494,549 A | 1/1985 | Namba et al. |
| 4,499,895 A | 2/1985 | Takayama |
| 4,505,272 A | 3/1985 | Utyamyshev et al. |
| 4,505,414 A | 3/1985 | Filipi |
| 4,520,817 A | 6/1985 | Green |
| 4,559,928 A | 12/1985 | Takayama |
| 4,573,468 A | 3/1986 | Conta et al. |
| 4,574,806 A | 3/1986 | McCarthy |
| 4,576,167 A | 3/1986 | Noiles |
| 4,589,412 A | 5/1986 | Kensey |
| 4,589,582 A | 5/1986 | Bilotti |
| 4,592,354 A | 6/1986 | Rothfuss |
| 4,592,498 A * | 6/1986 | Braun et al. ............... 227/121 |
| 4,593,679 A | 6/1986 | Collins |
| 4,603,693 A | 8/1986 | Conta et al. |
| 4,605,001 A | 8/1986 | Rothfuss et al. |
| 4,606,343 A | 8/1986 | Conta et al. |
| 4,610,383 A | 9/1986 | Rothfuss et al. |
| 4,631,052 A | 12/1986 | Kensey |
| 4,644,952 A | 2/1987 | Patipa et al. |
| 4,646,745 A | 3/1987 | Noiles |
| 4,655,673 A | 4/1987 | Hawkes |
| 4,667,673 A | 5/1987 | Li |
| 4,671,445 A | 6/1987 | Barker et al. |
| 4,672,961 A | 6/1987 | Davies |
| 4,674,515 A | 6/1987 | Andou et al. |
| 4,696,667 A | 9/1987 | Masch |
| 4,700,703 A | 10/1987 | Resnick et al. |
| 4,703,887 A | 11/1987 | Clanton et al. |
| 4,705,038 A | 11/1987 | Sjostrom et al. |
| 4,708,141 A | 11/1987 | Inoue et al. |
| 4,732,156 A | 3/1988 | Nakamura |
| 4,733,118 A | 3/1988 | Mihalko |
| 4,752,024 A | 6/1988 | Green et al. |
| 4,754,909 A | 7/1988 | Barker et al. |
| 4,756,309 A | 7/1988 | Sachse et al. |
| 4,760,840 A | 8/1988 | Fournier, Jr. et al. |
| 4,771,774 A | 9/1988 | Simpson et al. |
| 4,776,506 A | 10/1988 | Green |
| 4,781,186 A | 11/1988 | Simpson et al. |
| 4,784,137 A | 11/1988 | Kulik et al. |
| 4,789,090 A * | 12/1988 | Blake, III ................... 227/155 |
| 4,796,793 A * | 1/1989 | Smith et al. ................ 227/121 |
| 4,817,847 A | 4/1989 | Redtenbacher et al. |
| 4,819,632 A | 4/1989 | Davies |
| 4,821,942 A * | 4/1989 | Richards et al. ............ 227/132 |
| 4,867,158 A | 9/1989 | Sugg |
| 4,873,977 A | 10/1989 | Avant et al. |
| 4,887,599 A | 12/1989 | Muller |
| 4,892,244 A | 1/1990 | Fox et al. |
| 4,893,622 A | 1/1990 | Green et al. |
| 4,903,697 A | 2/1990 | Resnick et al. |
| 4,907,591 A | 3/1990 | Vasconcellos et al. |
| 4,917,114 A | 4/1990 | Green et al. |
| 4,928,699 A | 5/1990 | Sasai |
| 4,930,494 A | 6/1990 | Takehana et al. |
| 4,936,845 A | 6/1990 | Stevens |
| 4,955,882 A | 9/1990 | Hakky |
| 4,957,499 A | 9/1990 | Lipatov et al. |
| 4,962,877 A | 10/1990 | Hervas |
| 4,976,710 A | 12/1990 | Mackin |
| 4,994,060 A | 2/1991 | Rink et al. |
| 4,995,877 A | 2/1991 | Ams et al. |
| 5,005,749 A | 4/1991 | Aranyi |
| 5,040,715 A | 8/1991 | Green et al. |
| 5,059,203 A | 10/1991 | Husted |
| 5,071,430 A | 12/1991 | de Salis et al. |
| 5,077,506 A | 12/1991 | Krause |
| 5,100,041 A * | 3/1992 | Storace ..................... 227/116 |
| 5,104,025 A | 4/1992 | Main et al. |
| 5,114,065 A * | 5/1992 | Storace ..................... 227/132 |
| 5,133,359 A | 7/1992 | Kedem |
| 5,133,729 A | 7/1992 | Sjostrom |
| 5,139,513 A | 8/1992 | Segato |
| 5,170,925 A | 12/1992 | Madden et al. |
| 5,171,247 A | 12/1992 | Hughett et al. |
| 5,171,251 A | 12/1992 | Bregen et al. |
| 5,192,292 A | 3/1993 | Cezana et al. |
| 5,197,649 A | 3/1993 | Bessler et al. |
| 5,201,325 A | 4/1993 | McEwen et al. |
| 5,201,750 A | 4/1993 | Höcherl et al. |
| 5,205,459 A | 4/1993 | Brinkerhoff et al. |
| 5,207,691 A | 5/1993 | Nardella |
| 5,207,697 A | 5/1993 | Carusillo et al. |
| 5,237,884 A | 8/1993 | Seto |
| 5,249,583 A | 10/1993 | Mallaby |
| 5,258,007 A | 11/1993 | Spetzler et al. |
| 5,258,008 A | 11/1993 | Wilk |
| 5,261,877 A | 11/1993 | Fine et al. |
| 5,267,997 A | 12/1993 | Farin et al. |
| 5,268,622 A | 12/1993 | Philipp |
| 5,271,543 A | 12/1993 | Grant et al. |
| 5,271,544 A | 12/1993 | Fox et al. |
| 5,275,322 A | 1/1994 | Brinkerhoff et al. |
| 5,285,945 A | 2/1994 | Brinkerhoff et al. |
| 5,289,963 A | 3/1994 | McGarry et al. |
| 5,290,299 A | 3/1994 | Fain et al. |
| 5,292,053 A | 3/1994 | Bilotti et al. |

| | | | | | | |
|---|---|---|---|---|---|---|
| 5,312,023 | A | | 5/1994 | Green et al. | | |
| 5,318,221 | A | | 6/1994 | Green et al. | | |
| 5,326,013 | A | | 7/1994 | Green et al. | | |
| 5,330,486 | A | | 7/1994 | Wilk | | |
| 5,333,772 | A | * | 8/1994 | Rothfuss et al. | ............ | 227/120 |
| 5,333,773 | A | | 8/1994 | Main et al. | | |
| 5,350,104 | A | | 9/1994 | Main et al. | | |
| 5,383,880 | A | | 1/1995 | Hooven | | |
| 5,389,098 | A | | 2/1995 | Tsuruta et al. | | |
| 5,392,978 | A | * | 2/1995 | Velez et al. | .............. | 227/175.1 |
| 5,395,030 | A | | 3/1995 | Kuramoto et al. | | |
| 5,395,033 | A | | 3/1995 | Byrne et al. | | |
| D357,535 | S | | 4/1995 | Grant et al. | | |
| 5,403,312 | A | | 4/1995 | Yates et al. | | |
| 5,403,326 | A | | 4/1995 | Harrison et al. | | |
| 5,403,327 | A | | 4/1995 | Thornton et al. | | |
| 5,411,508 | A | | 5/1995 | Bessler et al. | | |
| 5,413,267 | A | | 5/1995 | Solyntjes | | |
| 5,425,738 | A | | 6/1995 | Gustafson et al. | | |
| 5,433,721 | A | | 7/1995 | Hooven et al. | | |
| 5,437,684 | A | | 8/1995 | Calabrese et al. | | |
| 5,441,507 | A | | 8/1995 | Wilk | | |
| 5,443,198 | A | | 8/1995 | Viola et al. | | |
| 5,454,825 | A | | 10/1995 | Van Leeuwen et al. | | |
| 5,467,911 | A | | 11/1995 | Tsuruta et al. | | |
| 5,474,223 | A | | 12/1995 | Viola et al. | | |
| 5,482,197 | A | | 1/1996 | Green et al. | | |
| 5,485,947 | A | | 1/1996 | Olson et al. | | |
| 5,518,163 | A | | 5/1996 | Hooven | | |
| 5,518,164 | A | | 5/1996 | Hooven | | |
| 5,529,235 | A | | 6/1996 | Boiarski et al. | | |
| 5,533,661 | A | | 7/1996 | Main et al. | | |
| 5,571,116 | A | | 11/1996 | Bolanos et al. | | |
| 5,588,579 | A | | 12/1996 | Schnut et al. | | |
| 5,609,285 | A | | 3/1997 | Grant et al. | | |
| 5,639,008 | A | | 6/1997 | Gallagher et al. | | |
| 5,653,374 | A | | 8/1997 | Young et al. | | |
| 5,667,517 | A | | 9/1997 | Hooven | | |
| 5,676,674 | A | | 10/1997 | Bolanos et al. | | |
| 5,709,335 | A | | 1/1998 | Heck | | |
| 5,732,872 | A | | 3/1998 | Bolduc et al. | | |
| 5,749,893 | A | | 5/1998 | Vidal et al. | | |
| 5,758,814 | A | | 6/1998 | Gallagher et al. | | |
| 5,779,130 | A | | 7/1998 | Alesi et al. | | |
| 5,782,396 | A | | 7/1998 | Mastri et al. | | |
| 5,782,397 | A | | 7/1998 | Koukline | | |
| 5,817,113 | A | | 10/1998 | Gifford, III et al. | | |
| 5,829,662 | A | * | 11/1998 | Allen et al. | .............. | 227/175.1 |
| 5,836,503 | A | | 11/1998 | Ehrenfels et al. | | |
| 5,868,760 | A | | 2/1999 | McGuckin, Jr. | | |
| 5,881,943 | A | | 3/1999 | Heck et al. | | |
| 5,897,562 | A | | 4/1999 | Bolanos et al. | | |
| 5,915,616 | A | | 6/1999 | Viola et al. | | |
| 5,947,363 | A | | 9/1999 | Bolduc et al. | | |
| 5,954,259 | A | | 9/1999 | Viola et al. | | |
| 5,957,363 | A | | 9/1999 | Heck | | |
| 5,976,159 | A | | 11/1999 | Bolduc et al. | | |
| 6,004,335 | A | | 12/1999 | Vaitekunas et al. | | |
| 6,119,913 | A | | 9/2000 | Adams et al. | | |
| 6,126,058 | A | | 10/2000 | Adams et al. | | |
| 6,174,324 | B1 | | 1/2001 | Egan et al. | | |

\* cited by examiner

TISSUE STAPLING ATTACHMENT FOR USE WITH AN ELECTROMECHANICAL DRIVER DEVICE

BACKGROUND OF THE INVENTION

1. Field of the Invention

The present invention relates generally to attachments for electromechanical driver devices, and more specifically to an attachment for an electromechanical driver device which may be used to staple tissue.

2. Description of the Prior Art

Upon identification of a region of herniated musculature in the abdominal wall, surgical intervention is almost always required. The procedure is straightforward in concept, but includes a number of technically sophisticated features, especially insofar as it is usually carried out remotely, i.e., through small portals formed in the patient's lower trunk. More particularly, the technique most often utilized involves forming two or three small puncture holes in the lower abdomen of the patient, inserting a corresponding cylindrical tube through each of the holes, passing elongate instruments through the tubes, retracting the soft tissues away from the site of the hernia, and stapling the torn tissue closed. This final closure step often further includes the use of a synthetic mesh, which is placed over the hole for the purpose of supporting the soft tissues and organs disposed above the healing hole. The mesh is stapled directly to the musculature, in the vicinity of the defect. The present invention is directed to the instrumentation which is the stapling component.

Traditional stapling mechanisms function in a simple manner. The staple is initially disposed in a U-shape. The staple driver component contacts the bottom portion of the staple and advances the two upwardly extending prongs of the staple through the items which are to be joined, and toward a stationary anvil portion. Often the items to be coupled require the anvil portion to be disposed behind them to provide adequate support so that the staple prongs may push through. Once the prongs of the staple have advanced through the items to be joined, the prongs contact the anvil. The anvil often comprises staple bending guide grooves formed therein for guiding the plastic deformation of the staples as they advance under the motivation of the staple driver. This plastic deformation bends (or folds) the staples toward one another in order to form the traditional box-shape from the original U-shape. The box-shaped staple is then pulled away from the stapling mechanism by virtue of its being coupled to the items it has joined.

Stapler devices utilized in laparoscopic and endoscopic surgery are significantly different than traditional stapling mechanisms in design and function. Unlike the traditional stapling mechanisms, a spatially distinct and opposing anvil portion is not practical and is therefore not used. Instead, the surgical stapler devices comprise an integrated staple driver and anvil component which holds and advances the staple into and through the tissue to be joined. More particularly, as shown in FIG. 1, the internal surgical tissue stapler devices of the prior art comprise an elongate tube 10 which is designed to slip through the portal tube of the minimally invasive entry hole. The tip 12 of the tube 10 includes a plurality of individual staples which are sequentially engaged by the staple driver. Each staple is initially disposed in a U-shape. The U-shape can be more specifically described by identifying the different regions thereof. The flat bottom portion of the staple has a central portion, and lateral portions. Upwardly extending prongs, which are disposed at the extreme lateral ends of the flat bottom portion, are each approximately equivalent in length, and are approximately equal to one third of the length of the flat bottom portion. The staple driver initially pushes the staple forward by pressing against the bottom portion of the staple at the central portion thereof. The staple is advanced forward until the prongs have extended beyond the tip of the housing, and have penetrated the tissue to be joined. Further advancement of the staple is prevented by an anvil portion which is fixed in the tip of the mechanism. The anvil, unlike the anvil of traditional stapling mechanisms, only contacts the central portion of the bottom portion of the staple, opposite the staple driver. Stated equivalently, once the staple has been advanced fully within the tip of the device, the anvil in the tip prevents the staple from moving forward as it becomes constrained between the staple driver on the back side and the anvil on the front.

At this time, a second mechanism is engaged in order to close the staple. This closing mechanism comprises a pair of straight tines which advance forward from within the tip, and contact the staple at the lateral portions of the bottom flat portion. The continued advancement of the prong bending tines causes the staple to deform as the prongs of the staple are forcibly turned toward one another. However, the actual site of the bending is not along the prongs. It is at the junction of the lateral and central portions of the flat bottom portion. This causes the fully deformed staple in this surgical stapler device to attain a D-shape as opposed to the B-shape which fully deformed staples of traditional stapling mechanisms attain. Release of the staple, once it has been coupled to the joined tissue, is achieved by first retracting the tines which bent the staple, and then twisting the shaft of the device to pull the staple off the anvil.

An additional feature of the surgical stapler devices of the prior art which should be appreciated in light of the present invention is the means by which all of the advancing elements, i.e., the staple driver and the prong bending tines, are motivated. In the minimally invasive surgical stapler devices of the prior art, the elongate tubular portion terminates in a handle which includes a trigger. The trigger has a dual function in that the compression of the trigger initially advances the staple driver without moving the prong bending tines. Once the staple has been fully advanced and is ready for bending, the tines are advanced through the tip to contact the staple, by continued compression of the grip-styled trigger.

It shall be easily recognizable that the requirement of manual triggering, as well as the two-step mechanism for advancing and then forming the staple, are both fraught with potential failures. In addition, the need to twist the shaft of the device to pull the staple off the anvil once the staple has joined the tissue presents a significant risk of tearing tissue as this action stresses both the staple and the tissue.

In addition, another drawback is that the mechanism for discharging the staples is a trigger coupled to a rigid elongate shaft which translates forward and backward in correspondence with the compression and release of the trigger. The rigidity of the shaft requires the surgeon to manipulate the entire device in order to align the stapler properly. Inasmuch as hernias of the abdominal cavity often occur on the floor of the abdomen, this manipulation is often quite difficult.

Finally, with regard to the use of the surgical stapler devices of the prior art, the devices are constructed to be completely disposable. The inability to re-use the devices increases the cost of using the devices. More specifically, this feature does not diminish the overall cost of manufacturing because of the obvious medical use requirements, but does increase the cost per procedure as a new device must be used for each surgery. In fact, if more staples are required for the surgery than are provided for in the device, an entirely new device must be used because there is no possibility of simply replacing the empty staple cartridge.

It is therefore a principal object of the present invention to provide a surgical stapler device which may be easily manipulated into the proper position without having to grossly deform the soft tissues through which the elongate shaft of the device passes.

It is also an object of the present invention to provide a surgical stapler device which has a single-step staple discharging mechanism.

It is a related object of the present invention to provide a surgical stapler device which does not stress surrounding tissue when the staple is released from the tip of the device.

It is an additional object of the present invention to provide a surgical stapler device which does not require the disposal of the tip and the staple driver, thereby minimizing the medical waste and cost associated with the use of the device as compared with surgical stapler devices of the prior art.

Other objects of the present invention shall be recognized in accordance with the description thereof provided hereinbelow, and in the Detailed Description of the Preferred Embodiment in conjunction with the remaining Figures.

SUMMARY OF THE INVENTION

The preceding objects of the invention are provided by a stapling attachment of the present invention which is coupleable to and remotely actuateable by an electromechanical driver device. In particular, the attachment couples at a proximal coupling end to a distal end of a flexible drive shaft of the electromechanical driver device, thereby coupling a threaded shaft of the attachment to a flexible draft shaft of the flexible shaft of the electromechanical driver device. As finger triggers actuated on the electromechanical driver device cause the flexible draft shaft to rotate, the threaded shaft rotates and advances in the housing of the attachment a threaded driver element of the attachment which tracks in the housing. Advancement of the threaded driver element advances a staple closing member mounted to the threaded driver element as well as a staple holding member coupled by a spring to the staple closing member. In this manner, a staple carried in a staple carrying groove of a staple carrying element of the staple holding member is advanced toward an opening of a distal staple discharging end of the attachment and into the tissue to be joined. After the staple has penetrated the tissue and the staple holding member contacts an opening lip formed in the opening of the distal staple discharging end, the spring compresses as the staple closing member continues to advance the staple toward the opening. Continued advancement of the staple closing mechanism pushes the staple against a groove lip of the staple carrying groove and protrusion tines of the staple closing member engage lateral portions of the flat bottom portion of the staple to close the prongs of the staple to form a D-shape and thereby join the tissue. Further advancement of the staple closing mechanism causes a sloping surface of the staple closing member to engage the flat bottom portion of the staple to force the staple out of the staple carrying groove to completely discharge and release the staple from the attachment. As finger triggers actuated on the electromechanical driver device cause the flexible draft shaft to reverse rotate, the threaded shaft reverse rotates and retracts the threaded driver element, causing the staple carrying element and the staple holding member to retract within the housing until the staple carrying element is returned to a staple receiving position adjacent a staple cartridge in the housing which contains a plurality of staples. When the staple carrying element is returned to this position, a staple from the plurality of staples is pushed from the staple cartridge into the staple carrying groove by a spring-loaded staple dispenser in functional communication with the staple cartridge, in preparation for a second stapling procedure.

More specifically, referring now to FIG. 2 with respect to the electromechanical driver device, an example embodiment of an electromechanical driver device 50 has a handle 52 and a flexible shaft 54. The handle 52 has a pistol grip-styled design, having a pair of finger triggers 58a,58b which are independently coupled to separate motors 60,62 coupled to and powered by a power source 64 and which each turn separate flexible drive shafts 78a,78b (described more fully hereinbelow). The motors 60,62 are each dual-direction motors, and are also coupled to a manual drive switch 66 mounted to the top of the handle 50, by which the user can selectively alter the turning direction of each motor 60,62. In this example, the power source 64 is a rechargeable battery pack providing a direct current.

The handle 50 further includes (1) a remote status indicator 68; (2) a flexible shaft steering means 70 and (3) an optional additional electrical supply (not shown). The remote status indicator 68 comprises an LCD or similar read-out device by which the user gains knowledge of the position of components (for example, whether the distal staple discharging end of the housing of the stapler attachment is in the proper position prior to the driving of the staples). Second, the handle 50 also includes a manually actuateable steering means 70, for example, a joystick or track ball, for directing the movement of the flexible shaft 72 (described more fully hereinbelow). Finally, the handle 50 may include an additional electrical power supply (not shown) and an on/off switch (not shown) for selectively supplying electrical power to attachments.

More particularly, with respect to the flexible shaft 72, the flexible shaft comprises a tubular sheath 74, preferably formed of a simple elastomeric material which is tissue compatible and which is sterilizable (i.e., is sufficiently rugged to withstand an autoclave). Various lengths of the flexible shaft 72 may be provided in conjunction with the present invention. In such a case, the flexible shaft 72 and the handle 50 should be separable and such that the interface between the proximal end of the flexible shaft 72 and the distal end of the handle 50 includes a coupling means for the drive components. Specifically regarding the drive components of the flexible shaft 72, within the elastomeric sheath are a pair of smaller fixed tubes 76a,76b which each contain a flexible drive shaft 78a,78b which is capable of rotating within the corresponding fixed tube 76a,76b. Each flexible drive shaft 78a,78b itself is capable of translating a torque from the corresponding drive motor 60,62 in the handle 50 to the distal end 80 of the flexible shaft 72, while still being flexible enough to be bent, angled, curved, etc. as the surgeon deems necessary to "snake" the flexible shaft 72 through the bowel of the patient. For example, the flexible drive shafts 78a,78b may comprise a woven steel fiber cable. It shall be recognized that other flexible drive shafts may be suitable for this purpose. In order for the distal end 80 of the flexible shaft 72 to couple with an attachment, such as the stapling attachment of the present invention (as described more fully hereinbelow), the distal tips 82a,82b of the flexible drive shafts 78a,78b have a conformation which permits the continued translation of torque. For example, the distal tips 82a,82b of the flexible drive shafts 78a,78b are hexagonal, thereby fitting into a socket, or hexagonal recess, of the proximal coupling end of the housing of the stapler attachment. As suggested above, in conjunction with the manually actuatable steering means 70 mounted to the handle 50, the flexible shaft 72 further includes at least two steering wires 84 which are flexible, but are coupled to the inner surface of the flexible shaft 72 near the distal end 80 thereof. The steering wires 84 may be axially translated relative to one another by actuation of the manually actuatable steering means 70, which action causes the flexible shaft 72 to bend and curve accordingly. Also, as suggested above, in conjunction with the remote status indicator 68 of the handle 50, the flexible shaft 72 further contains an electrical lead 86 for coupling to the attachments. This electrical lead 86 channels a signal from the attachment to the handle 50 for indicating the status of the attachment (for example, indicating whether the tissue to be joined is adjacent to the distal staple discharging end of the stapling attachment, or indicating the number of staples left in the staple cartridge). Similarly, additional electrical leads may be provided to supply power to separate aspects of the attachment if so required.

More particularly, with respect to the stapling attachment of the present invention, the attachment comprises a housing having a distal staple discharging end and a proximal coupling end which has a socket for coupling the attachment to the distal end of the flexible shaft. The distal staple discharging end has an opening through which the staples are sequentially discharged, and an opening lip formed in the opening. The attachment further comprises a threaded shaft which engages the flexible draft shaft of the flexible shaft of the electromechanical driver device when the proximal coupling end is coupled to the distal end of the flexible shaft, such that the threaded shaft rotates in correspondence with the rotation of the flexible draft shaft of the flexible shaft. The threaded shaft has, mounted thereabout, a threaded driver element which is similar in structure to a nut, but which is tracked within the housing so that rotation of the threaded shaft causes the threaded driver element to advance or retract along the threaded shaft within the housing of the attachment.

The attachment further comprises a staple holding member, a staple carrying element integral with said staple holding member, and an anvil portion integral with the staple carrying element. The attachment further comprises a staple closing member concentrically mounted about the staple holding member. The staple holding member and the staple closing member are coupled together by a spring and mounted to the threaded driver element such that advancement of the threaded driver element advances the staple holding member and the staple closing member. The staple closing member comprises a pair of protrusions, or protruding tines which are positioned to engage the staple at the lateral portions of the flat bottom portion of the staple. The staple closing member further comprises a sloped surface which is adapted to engage the central portion of the flat bottom portion of the staple. The staple carrying element comprises an angled staple carrying groove having the anvil portion, or groove lip.

The attachment further comprises a replaceable staple cartridge mounted to the housing of the attachment. The staple cartridge contains a plurality of staples. The staple cartridge is in functional communication with a spring-loaded staple dispenser.

When the proximal coupling end of the housing of the stapling attachment is coupled to the distal end of the flexible shaft of the electromechanical driver device, the threaded shaft of the stapling attachment engages the flexible draft shaft of the flexible shaft. Remote actuation of the flexible draft shaft using a first finger trigger of the electromechanical driver device causes the flexible draft shaft to rotate, which in turn causes the threaded shaft to rotate, which causes the threaded driver element to advance within the housing of the attachment. Alternate remote actuation of the flexible draft shaft using a second finger trigger causes the flexible draft shaft to reverse rotate, which in turn causes the threaded shaft to reverse rotate, which causes the threaded driver element to retract within the housing of the attachment. Thus, as stated above, the staple holding member and the staple carrying element advance and retract with the threaded driver element. When the staple carrying element is retracted into a staple receiving position, adjacent to the staple cartridge, a staple is pushed by the spring-loaded staple dispenser from the staple cartridge into the staple carrying groove of the staple carrying element. As the staple holding member and the staple closing member advance within the housing, the staple is carried within the staple carrying groove. The angle of the staple carrying groove ensures that the staple remains in the staple carrying groove during this advancement. The staple is carried to the distal staple discharging end of the housing and the prongs of the staple are inserted into the tissue to be joined. After the prongs have penetrated the tissue, the opening lip of the distal staple discharging end stops the staple holding member. Upon continued advancement of the threaded driver element, the spring which couples the staple closing member and the staple holding member compresses, causing the staple closing member to further advance. As the staple closing member further advances, the protruding tines engage the staple at the lateral portions of the flat bottom portion of the staple, press the staple against the groove lip of the staple carrying groove, and bend the lateral portions of the flat bottom portion of the staple to close the prongs of the staple to form a D-shape and thereby join the tissue. Upon continued advancement of the threaded driver element, the staple closing member further advances, and the sloped surface of the staple closing member engages the central portion of the flat bottom portion of the staple to force the staple out of the staple carrying groove to completely discharge and release the staple from the attachment. Thereafter, the threaded driver element is retracted, causing the staple carrying element and the staple holding member to retract within the housing. When the staple carrying element is returned to a staple receiving position, adjacent to the staple cartridge, a second staple is pushed by the spring-loaded staple dispenser from the staple cartridge into the staple carrying groove of the staple carrying element in preparation for a second stapling procedure.

DETAILED DESCRIPTION OF THE PREFERRED EMBODIMENTS

Figure 3:
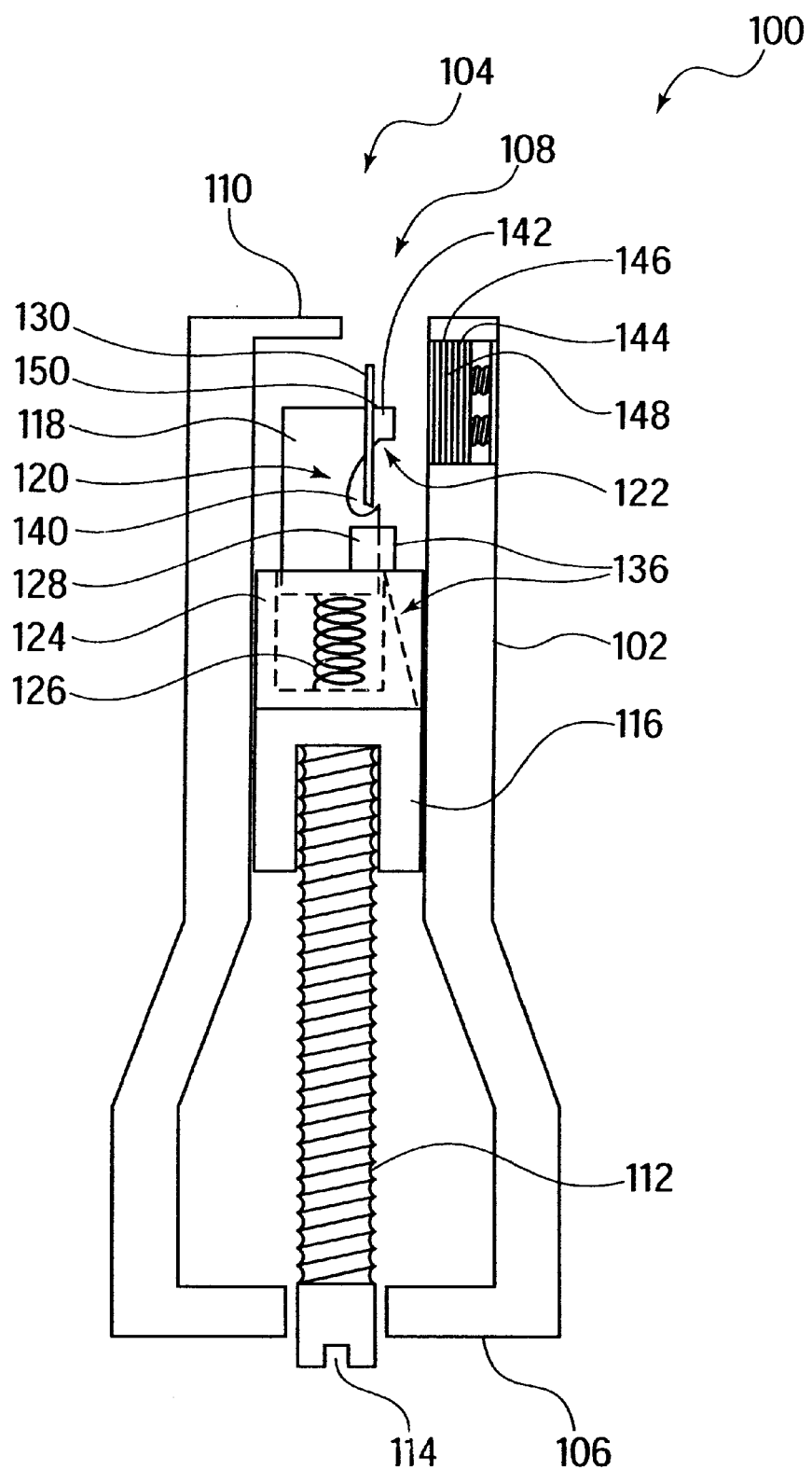
FIG. 3 is a side cross-sectional view of a stapling attachment of the present invention, in which the staple holding member and the staple carrying element are in a staple-loading position.
Figure 4:
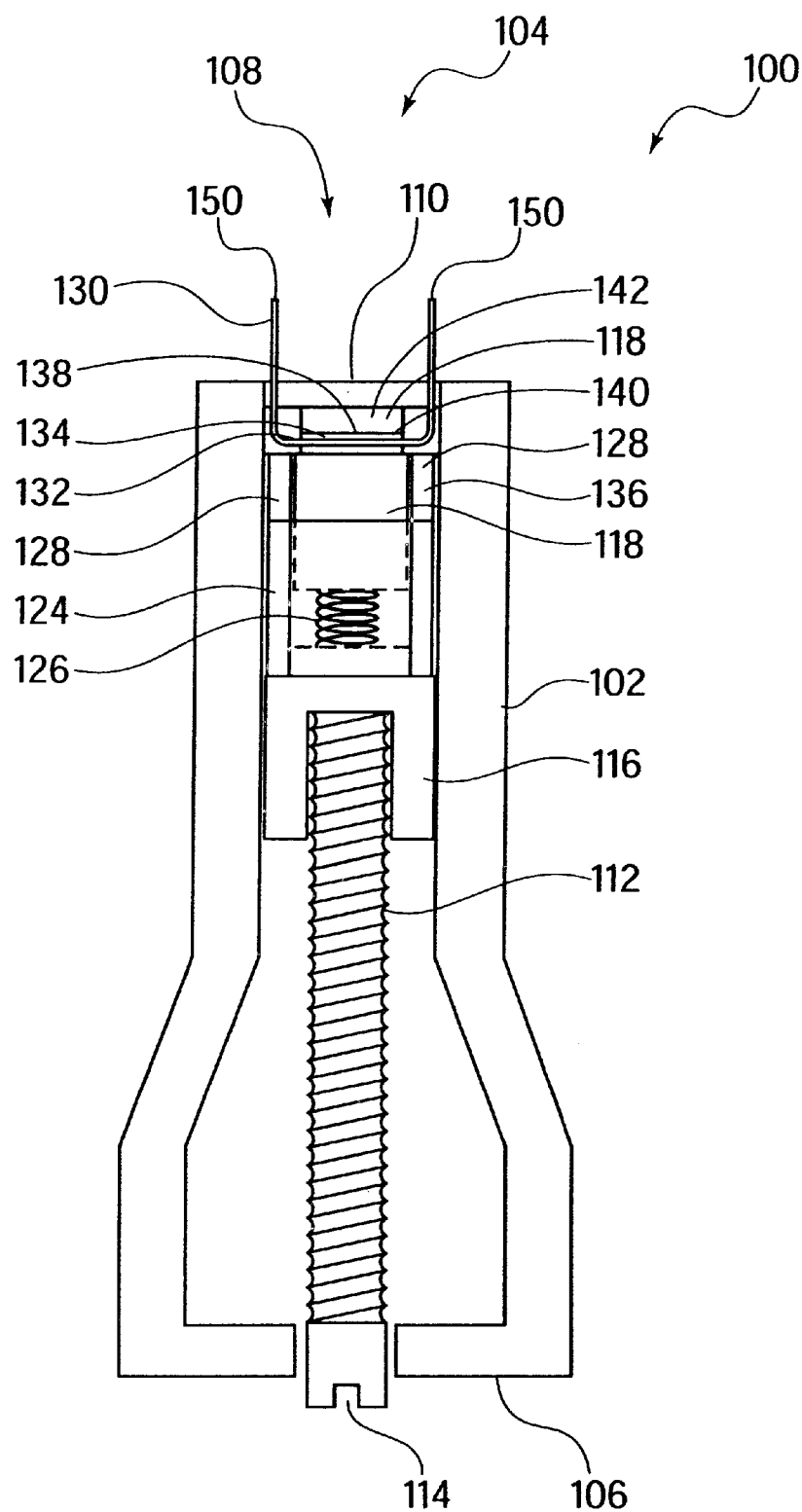
FIG. 4 is a side cross-sectional view of a stapling attachment of the present invention (turned 90 degrees with respect to FIG. 3), in which the staple holding member and the staple carrying element are in a staple-discharging disposition.

As set forth above, the present invention comprises a tissue stapling attachment for use with an electromechanical driver device. More particularly, and referring now to FIGS. 3 and 4, a preferred embodiment of the attachment 100 comprises a housing 102 having a distal staple discharging end 104 and a proximal coupling end 106 which has a socket 114 for coupling the attachment 100 to the distal end (best shown as item 80 of FIG. 2) of the flexible shaft (best shown as item 72 of FIG. 2) of the electromechanical driver device (best shown in FIG. 2). (Generally see co-pending U.S. patent application Ser. No. 09/324,452, entitled "An Electromechanical Driver Device For Use With Anastomosing, Stapling, and Resecting Instruments".) The distal staple discharging end 104 has an opening 108 through which the staples are sequentially discharged, and an opening lip 110 formed in the opening 108. The attachment 100 further comprises a threaded shaft 112 which engages the flexible draft shaft (best shown as item 78a or item 78b of FIG. 2) of the flexible shaft when the proximal coupling end 106 is coupled to the distal end of the flexible shaft, such that the threaded shaft 112 rotates in correspondence with the rotation of the flexible draft shaft of the flexible shaft. The threaded shaft 112 has, mounted thereabout, a threaded driver element 116 which is similar in structure to a nut, but which is tracked within the housing 102 so that rotation of the threaded shaft 112 causes the threaded driver element 116 to advance or retract along the threaded shaft 112 within the housing 102 of the attachment 100.

The attachment 100 further comprises a staple holding member 118, a staple carrying element 120 integral with said staple holding member 118, and an anvil portion 122 integral with the staple carrying element 120. The attachment 100 further comprises a staple closing member 124 concentrically mounted about the staple holding member 118. The staple holding member 118 and the staple closing member 124 are coupled together by a spring 126 and mounted to the threaded driver element 116 such that advancement of the threaded driver element 116 advances the staple holding member 118 and the staple closing member 124. The staple closing member 124 comprises a pair of protrusions, or protruding tines 128 which are positioned to engage the staple 130 at the lateral portions 132 (best shown on FIG. 4) of the flat bottom portion 134 (best shown on FIG. 4) of the staple 130. The staple closing member 124 further comprises a sloped surface 136 which is adapted to engage the central portion 138 (best shown on FIG. 4) of the flat bottom portion 134 of the staple 130. The staple carrying element 120 comprises an angled staple carrying groove 140 having the anvil portion, or groove lip 142.

The attachment 100 further comprises a replaceable staple cartridge 144 mounted to the housing 102 of the attachment 100. The staple cartridge 144 contains a plurality of staples 146. The staple cartridge 144 is in functional communication with a spring-loaded staple dispenser 148.

Figure 1:
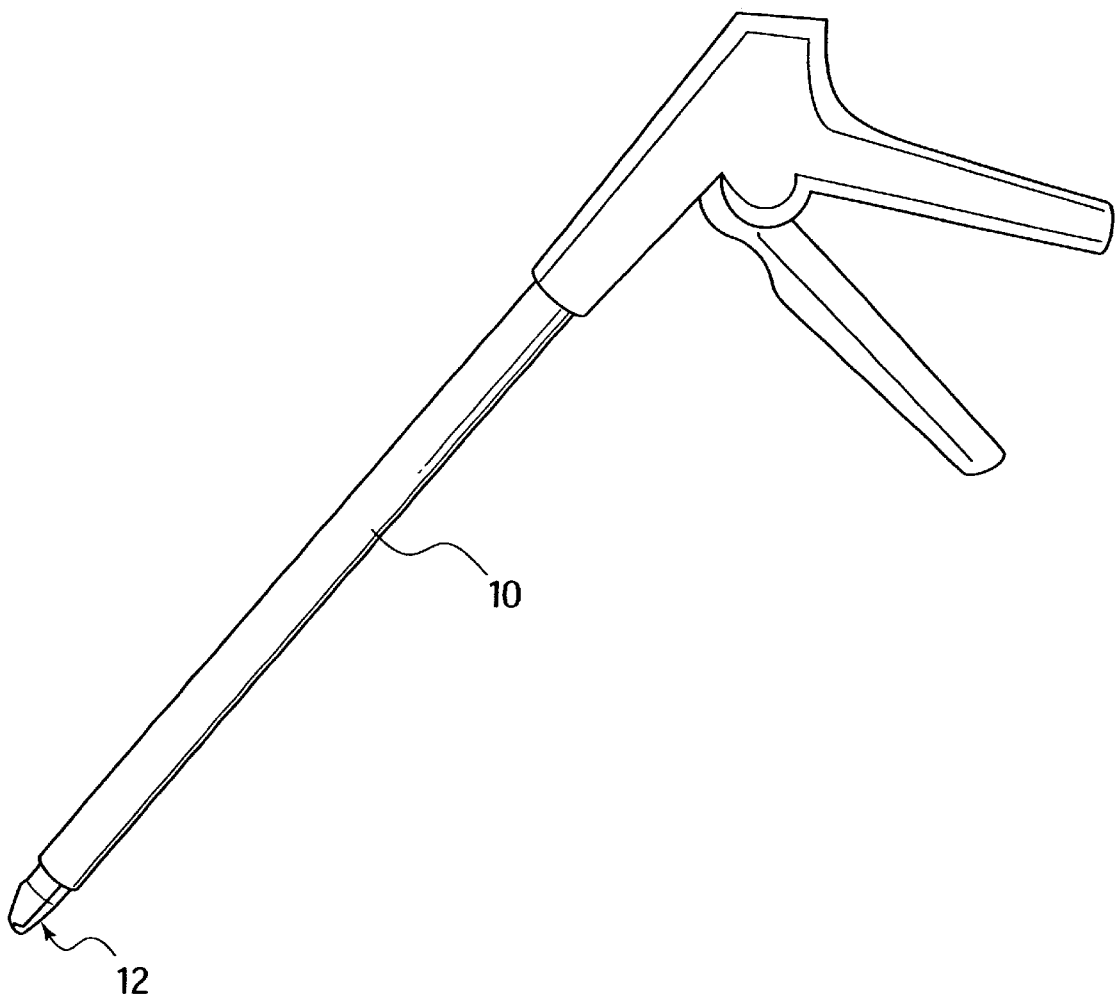
FIG. 1 is a perspective view of a surgical stapler device of the prior art.
Figure 2:
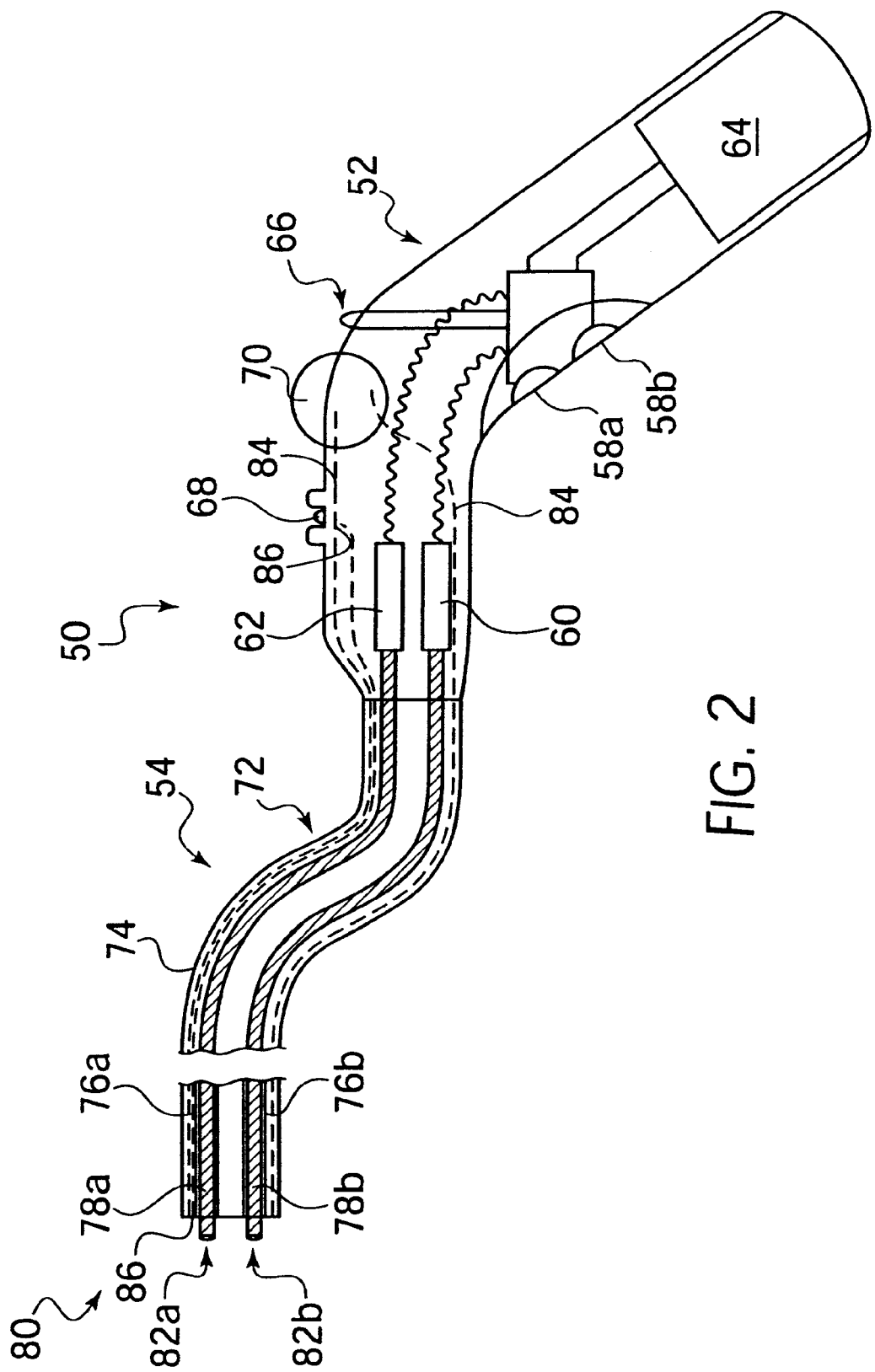
FIG. 2 is a perspective view of an electromechanical driver device for use with the present invention.

In operation, when the proximal coupling end 106 of the housing 102 of the stapling attachment 100 is coupled to the distal end of the flexible shaft of the electromechanical driver device (best shown in FIG. 2), the threaded shaft 112 of the stapling attachment 100 engages the flexible draft shaft (best shown as item 78a or item 78b on FIG. 2) of the flexible shaft (best shown as item 72 on FIG. 2). Remote actuation of the flexible draft shaft using a finger trigger (best shown as item 58a or item 58b on FIG. 2) of the electromechanical driver device causes the flexible draft shaft to rotate, which in turn causes the threaded shaft 112 to rotate, which causes the threaded driver element 116 to advance within the housing 102 of the attachment 100. Remote switching of the manual drive switch (best shown as item 66 on FIG. 2) of the electromechanical driver device and subsequent remote actuation of the finger trigger of the electromechanical driver device causes the flexible draft shaft to reverse rotate, which in turn causes the threaded shaft 112 to reverse rotate, which causes the threaded driver element 116 to retract within the housing 102 of the attachment 100. Thus, as stated above, the staple holding member 118 and the staple carrying element 120 advance and retract with the threaded driver element 116. When the staple carrying element 120 is retracted into a staple receiving position, adjacent to the staple cartridge 144, a staple from the plurality of staples 146 is pushed by the spring-loaded staple dispenser 148 from the staple cartridge 144 into the staple carrying groove 140 of the staple carrying element 120. As the staple holding member 118 and the staple closing member 124 advance within the housing 102, the staple 130 is carried within the staple carrying groove 140. The angle of the staple carrying groove 140 ensures that the staple 130 remains in the staple carrying groove 140 during this advancement. The staple 130 is carried to the distal staple discharging end 104 of the housing 102 and the prongs 150 (best shown on FIG. 4) of the staple 130 are inserted into the tissue to be joined. After the prongs 150 have penetrated the tissue, the opening lip 110 of the distal staple discharging end 104 stops the staple holding member 118. Upon continued advancement of the threaded driver element 116, the spring 126 which couples the staple closing member 124 and the staple holding member 118 compresses, causing the staple closing member 124 to further advance. As the staple closing member 124 further advances, the protruding tines 128 engage the staple 130 at the lateral portions 132 (best shown on FIG. 4) of the flat bottom portion 134 (best shown on FIG. 4) of the staple 130, press the staple 130 against the groove lip 142 of the staple carrying groove 140, and bend the lateral portions 132 of the flat bottom portion 134 of the staple 130 to close the prongs 150 of the staple 130 to form a D-shape and thereby join the tissue. Upon continued advancement of the threaded driver element 116, the staple closing member 124 further advances, and the sloped surface 136 of the staple closing member 124 engages the central portion 138 of the flat bottom portion 134 of the staple 130 to force the staple 130 out of the staple carrying groove 140 to completely discharge and release the staple 130 from the attachment 100. Thereafter, the threaded driver element 116 is retracted, causing the staple carrying element 120 and the staple holding member 118 to retract within the housing 102. When the staple carrying element 120 is returned to a staple receiving position, adjacent to the staple cartridge 144, a second staple is pushed into the staple carrying groove 140 of the staple carrying element 120 in preparation for a second stapling procedure.

What is claimed is:

1. An electro-mechanical surgical system, comprising:
   an elongated shaft;
   an axially rotatable drive shaft disposed within the elongated shaft;
   a surgical device configured to detachably couple to a distal end of the elongated shaft, wherein the device includes:

a housing having an opening and an opening lip formed in the opening;

a driver disposed in the housing;

a staple closing member mounted to the driver and translating within the housing in correspondence with the driver; and a staple holding member configured to hold a staple and coupled by a spring to the staple closing member, wherein the driver is configured to advance the staple closing member and the staple holding member toward the opening and advances the staple into tissue to be joined until further advancement of the staple holding member is prevented by contact between the staple holding member and the opening lip, wherein the driver is further configured to advance the staple closing member as the spring is compressed and to cause the staple closing member to close the staple within the tissue; and a motor system configured to drive the axially rotatable drive shaft.

2. The electro-mechanical surgical system according to claim 1, wherein the driver includes a threaded rotatable shaft configured to be coupled to the axially rotatable shaft.

3. An electro-mechanical surgical system, comprising:

an elongated shaft;

an axially rotatable drive shaft disposed within the elongated shaft;

a surgical device configured to detachably couple to a distal end of the elongated shaft, wherein the device includes a housing having an opening and an opening lip formed in the opening;

a driver disposed in the housing;

a staple closing member mounted to the driver and translating within the housing in correspondence with the driver; and a staple holding member configured to hold a staple and coupled by a spring to the staple closing member, wherein the driver is configured to advance the staple closing member and the staple holding member toward the opening and advances the staple into tissue to be joined until further advancement of the staple holding member is prevented by contact between the staple holding member and the opening lip, wherein the driver is further configured to advance the staple closing member as the spring is compressed and to cause the staple closing member to close the staple within the tissue; and a motor system configured to drive the axially rotatable drive shaft;

a control system configured to control the motor system; and a remote control unit configured to communicate with the control system to control the motor system via the control system.

4. The electro-mechanical surgical system according to claim 3, wherein the remote control unit includes a wired remote control unit.

5. An electro-mechanical surgical system, comprising:

an elongated shaft;

an axially rotatable drive shaft disposed within the elongated shaft;

a surgical device configured to detachably couple to a distal end of the elongated shaft, wherein the device includes:

a housing having an opening and an opening lip formed in the opening;

a driver disposed in the housing;

a staple closing member mounted to the driver and translating within the housing in correspondence with the driver; and a staple holding member configured to hold a staple and coupled by a spring to the staple closing member, wherein the driver is configured to advance the staple closing member and the staple holding member toward the opening and advances the staple into tissue to be joined until further advancement of the staple holding member is prevented by contact between the staple holding member and the opening lip, wherein the driver is further configured to advance the staple closing member as the spring is compressed and to cause the staple closing member to close the staple within the tissue, wherein a staple is loaded into the staple holding member through the use of a spring-loaded mechanism when the staple holding member is in a staple receiving position within the housing; and a motor system configured to drive the axially rotatable drive shaft.

6. An electro-mechanical surgical system, comprising:

an elongated shaft;

an axially rotatable drive shaft disposed within the elongated shaft;

a surgical device configured to detachably couple to a distal end of the elongated shaft, wherein the device includes:

a housing having an opening and an opening lip formed in the opening;

a driver disposed in the housing;

a staple closing member mounted to the driver and translating within the housing in correspondence with the driver; and a staple holding member configured to hold a staple and coupled by a spring to the staple closing member, wherein the driver is configured to advance the staple closing member and the staple holding member toward the opening and advances the staple into tissue to be joined until further advancement of the staple holding member is prevented by contact between the staple holding member and the opening lip, wherein the driver is further configured to advance the staple closing member as the spring is compressed and to cause the staple closing member to close the staple within the tissue, wherein a staple is loaded into the staple holding member when the staple holding member is in a staple receiving position within the housing, and wherein the staple, before being loaded into the staple holding member, is held in a staple cartridge and is loaded into the staple holding member by being pushed from the staple cartridge into the staple holding member; and a motor system configured to drive the axially rotatable drive shaft.

7. An electro-mechanical surgical system, comprising:

an elongated shaft;

an axially rotatable drive shaft disposed within the elongated shaft;

a surgical device configured to detachably couple to a distal end of the elongated shaft, wherein the device includes:

a housing having an opening and an opening lip formed in the opening;

a driver disposed in the housing;

a staple closing member mounted to the driver and translating within the housing in correspondence with the driver; and a staple holding member configured to hold a staple and coupled by a spring to the staple closing member, wherein the driver is configured to advance the staple closing member and the staple holding member toward the opening and advances the staple into tissue to be joined until further advancement of the staple holding member is prevented by contact between the staple holding member and the opening lip, wherein the driver is further configured to advance the staple closing member as the spring is compressed and to cause the staple closing member to close the staple within the tissue, and wherein the staple holding member includes a staple carrying groove within which a staple is carried during advancement of the staple holding member, the staple carrying groove having a groove lip against which a flat bottom portion of the staple is pressed by the staple closing member after the staple holding member comes into contact with the opening lip; and a motor system configured to drive the axially rotatable drive shaft.

8. The electro-mechanical surgical system according to claim 7, wherein the stapling closing member includes protrusions that engage lateral portions of the flat bottom portion of staple.

9. The electro-mechanical surgical system according to claim 7, wherein the staple closing member includes a sloped surface that engages a central portion of a flat bottom portion of a staple, and wherein, after the staple has closed within the tissue, continued advancement of the driver causes the sloped surface to push the staple out of the staple carrying groove.

10. A surgical stapler, comprising:

a housing having an opening, a lip being formed in the opening;

a staple closing member advancing longitudinally within said housing;

a staple holding member configured to hold a staple;

a spring positioned between the staple closing member and the staple holding member; and a rotatable drive shaft coupled to the staple closing member, wherein rotation of the drive shaft advances the staple holding member and staple closing member until further advancement of the staple holding member is prevented by contact between the staple holding member and the lip, wherein continued rotation of the drive shaft further advances said staple closing member so that the staple closing member compresses the spring and closes the staple while the staple holding member is prevented from further advancement.

11. The surgical stapler according to claim 10, wherein the staple closing member has a sloped surface, and wherein continued rotation of the drive shaft advances the staple closing member so that the sloped surface engages the staple and releases the staple from the staple holding member.

* * * * *